US00PP18929P2

(12) United States Plant Patent
Smith

(10) Patent No.: US PP18,929 P2
(45) Date of Patent: Jun. 10, 2008

(54) ***CHRYSANTHEMUM* PLANT NAMED 'SLY YOJENNA'**

(50) Latin Name: *Chrysanthemum×morifolium*
Varietal Denomination: Sly Yojenna

(75) Inventor: Mark A. Smith, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/641,536

(22) Filed: Dec. 18, 2006

(51) Int. Cl.
*A01H 5/00* (2006.01)

(52) U.S. Cl. ..... Plt./293
(58) Field of Classification Search ..... Plt./293
See application file for complete search history.

(56) References Cited

U.S. PATENT DOCUMENTS

PP16,134 P2 * 11/2005 Smith ..... Plt./293
PP17,532 P2 * 3/2007 Smith ..... Plt./292

* cited by examiner

*Primary Examiner*—Wendy C. Haas
(74) *Attorney, Agent, or Firm*—C. A. Whealy

(57) ABSTRACT

A new and distinct cultivar of *Chrysanthemum* plant named 'Sly Yojenna', characterized by its compact, upright and outwardly spreading plant habit; freely branching habit; dense and full plant habit; uniform and freely flowering habit; decorative-type inflorescences with elongated oblong to ligulate-shaped ray florets, red purple-colored ray florets; and natural season flowering about September 26$^{th}$ in the Northern Hemisphere.

1 Drawing Sheet

Botanical designation: *Chrysanthemum×morifolium.*
Cultivar denomination: 'Sly Yojenna'.

BACKGROUND OF THE INVENTION

The present invention relates to a new and distinct cultivar of *Chrysanthemum* plant, botanically known as *Chrysanthemum×morifolium,* commercially grown as a garden *Chrysanthemum* and hereinafter referred to by the name 'Sly Yojenna'.

The objective of the breeding program is to create new garden-type *Chrysanthemum* cultivars having inflorescences with desirable inflorescence forms, attractive floret colors and good garden performance.

The new *Chrysanthemum* is a naturally-occurring whole plant mutation of the *Chrysanthemum×morifolium* cultivar Yojenna, disclosed in U.S. Plant Pat. No. 17,532. The new *Chrysanthemum* was discovered and selected by the Inventor as a single flowering plant within a population of plants of the parent selection in December, 2003, in Alva, Fla. The selection of this plant was based on its desirable inflorescence color and good form and substance.

Asexual reproduction of the new *Chrysanthemum* by vegetative cuttings was first conducted in Alva., Fla. in February, 2004. Asexual reproduction by cuttings has shown that the unique features of this new *Chrysanthemum* are stable and reproduced true to type in successive generations.

SUMMARY OF THE INVENTION

Plants of the cultivar Sly Yojenna have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sly Yojenna'. These characteristics in combination distinguish 'Sly Yojenna' as a new and distinct garden *Chrysanthemum* cultivar:

1. Compact, upright and outwardly spreading plant habit.
2. Freely branching habit; dense and full plant habit.
3. Uniform and freely flowering habit.
4. Decorative-type inflorescences with elongated oblong to ligulate-shaped ray florets.
5. Red purple-colored ray florets.
6. Natural season flowering about September 26$^{th}$ in the Northern Hemisphere.

In side-by-side comparisons conducted in Alva, Fla., plants of the new *Chrysanthemum* differed primarily from plants of the parent, the cultivar Yojenna, in ray floret color as ray florets of plants of the new *Chrysanthemum* were more red in color than ray florets of plants of the cultivar Yojenna.

Plants of the new *Chrysanthemum* can be compared to plants of the *Chrysanthemum* cultivar Yobrandi, disclosed in U.S. Plant Pat. No. 16,134. In side-by-side comparisons conducted in Alva, Fla., plants of the new *Chrysanthemum* differed from plants of the cultivar Yobrandi in the following characteristics:

1. Plants of the new *Chrysanthemum* were taller and more upright than plants of the cultivar Yobrandi.
2. Plants of the new *Chrysanthemum* had larger inflorescences than plants of the cultivar Yobrandi.
3. Ray florets of plants of the new *Chrysanthemum* were lighter red in color than ray florets of plants of the cultivar Yobrandi.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph at the bottom of the sheet comprises a side perspective view of a typical flowering plant of 'Sly Yojenna'.

The photograph at the top of the sheet is a close-up view of typical inflorescences of 'Sly Yojenna'.

DETAILED BOTANICAL DESCRIPTION

The aforementioned photographs and following observations and measurements describe plants grown in Fletcher, N.C. during the summer in an outdoor nursery and under conditions and practices which approximate those generally used in commercial garden *Chrysanthemum* production. During the production of the plants, day temperatures averaged 29° C. and night temperatures averaged 16° C. Plants were grown in 15-containers, exposed to long day/short night conditions and pinched about two weeks later. About two weeks after the pinch, the photoinductive short day/long night treatments were started. Plants used in the photographs and for the description were about three months old. In the following description, color references are made to The Royal Horticultural Society Colour Chart, 1995 Edition, except where general terms of ordinary dictionary significance are used.

Botanical classification: *Chrysanthemum×morifolium* cultivar Sly Yojenna.

Parentage: Naturally-occurring whole plant mutation of the *Chrysanthemum×morifolium* cultivar Yojenna, disclosed in U.S. Plant Pat. No. 17,532.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Herbaceous decorative-type garden *Chrysanthemum.* Stems upright and outwardly spreading giving a uniformly mounded appearance to the plant. Freely branching habit, about four to five lateral branches develop after removal of terminal apex (pinching) each with numerous secondary laterals; dense and full plant habit. Strong and vigorous growth habit.

*Plant height.*—About 26 cm.

*Plant width.*—About 31 cm.

*Lateral branches.*—Length: About 24 cm. Diameter: About 8.5 mm. Internode length: About 1.2 cm. Strength: Strong. Texture: Pubescent. Color: 148C.

*Leaves.*—Arrangement: Alternate, simple. Length: About 5 cm. Width: About 4.7 cm. Apex: Broadly acute. Base: Obtuse with truncate tendencies. Margins: Palmately lobed, sinuses between lateral lobes mostly parallel. Texture, upper and lower surfaces: Fine pubescence; veins prominent on lower surface. Color: Developing and fully expanded foliage, upper surface: 147A; venation, 147B. Developing and fully expanded foliage, lower surface: 147B; venation, 147C. Petiole: Length: About 2 cm. Diameter: About 2.5 mm. Texture, upper and lower surfaces: Pubescent. Color, upper and lower surfaces: 147B.

Inflorescence description:

*Appearance.*—Decorative-type inflorescence form with elongated oblong to ligulate-shaped ray florets. Inflorescences borne on terminals above foliage. Disk and ray florets arranged acropetally on a capitulum. Inflorescences faintly fragrant.

*Flowering response.*—Under natural season conditions, plants flower about September 26$^{th}$ in the Northern Hemisphere. At other times of the year, inflorescence initiation and development can be induced under short day/long night conditions (at least 13.5 hours of darkness). Early flowering habit; plants exposed to photoinductive short day/long night conditions flower about 51 days later.

*Postproduction longevity.*—Inflorescences maintain good color and substance for about 3.5 weeks in an outdoor nursery.

*Quantity of inflorescences.*—About 27 to 28 inflorescences develop per lateral branch.

*Inflorescence bud.*—Height: About 1.3 cm. Diameter: About 1.1 cm. Shape: Ovoid. Color: 53A.

*Inflorescence size.*—Diameter: About 4.7 cm. Depth (height): About 1.8 cm. Disc diameter: About 5 mm; inconspicuous. Receptacle diameter: About 1.6 cm. Receptacle height: About 5 mm.

*Ray florets.*—Shape: Elongated-oblong to ligulate. Orientation: Initially upright, then about 45° to 60° from vertical; eventually perpendicular to peduncle. Aspect: Initially incurved, then mostly concave. Length: About 2.3 cm. Width: About 7 mm. Apex: Slightly emarginate. Base: Acute. Margin: Entire. Texture, upper and lower surfaces: Smooth, glabrous, satiny. Number of ray florets per inflorescence: About 150 arranged in about 12 to 14 whorls. Color: When opening, upper surface: 53A. When opening, lower surface: 182B to 182C. Fully opened, upper surface: 59A to 59B; color becoming closer to 180A with development. Fully opened, lower surface: 183D; color becoming closer to 179C to 179D with development.

*Disc florets.*—Shape: Tubular, elongated. Length: About 6 mm. Diameter: About 2 mm. Number of disc florets per inflorescence: About 13. Color, immature: Apex: Close to 14A. Mid-section: Close to 10D. Base: Close to 157A. Color, mature: Apex: Close to 12A. Mid-section: Close to 1D. Base: Close to 157A.

*Phyllaries.*—Number of phyllaries per inflorescence: About 18 arranged in about one or two whorls. Length: About 8 mm. Width: About 4 mm. Shape: Elliptic. Apex: Acute. Base: Truncate. Texture, upper surface: Smooth, waxy. Texture, lower surface: Pubescent. Color, upper surface: Close to 137B. Color, lower surface: Close to 137A.

*Peduncles.*—Length: About 3.7 cm. Diameter: About 3 mm. Angle: About 45° from vertical. Strength: Strong. Texture: Pubescent; longitudinally ridged. Color: Close to 148A.

*Reproductive organs.*—Androecium: Stamen number: About five per floret. Filament length: About 1 mm. Filament color: Close to 1C. Anther length: Less than 1 mm. Anther shape: Oblong. Anther color: Close to 12A. Pollen amount: None observed. Gynoecium: Pistil length: About 6 mm. Stigma shape:

Bi-parted. Stigma color: Close to 2C. Style length: About 3 mm. Style color: Close to 2C. Ovary color: Close to 157D.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and to tolerate temperatures from about 0° C. to about 38° C.

It is claimed:

1. A new and distinct *Chrysanthemum* plant named 'Sly Yojenna' as illustrated and described.

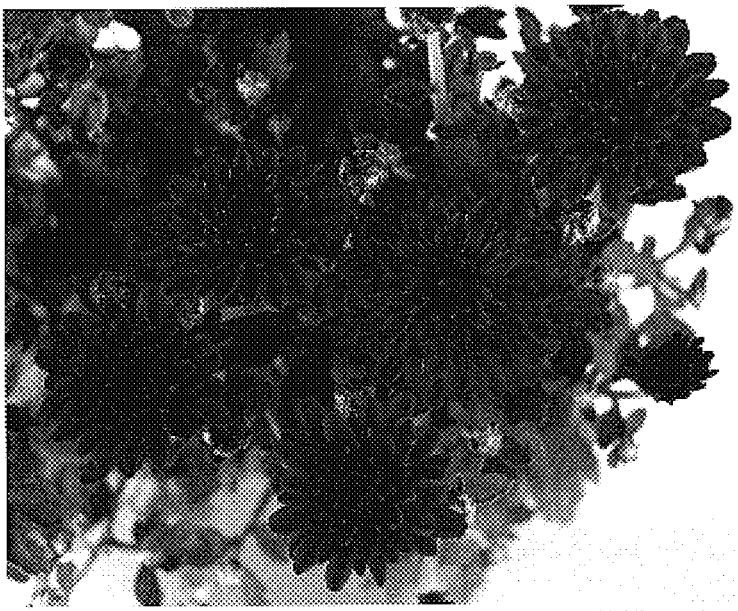
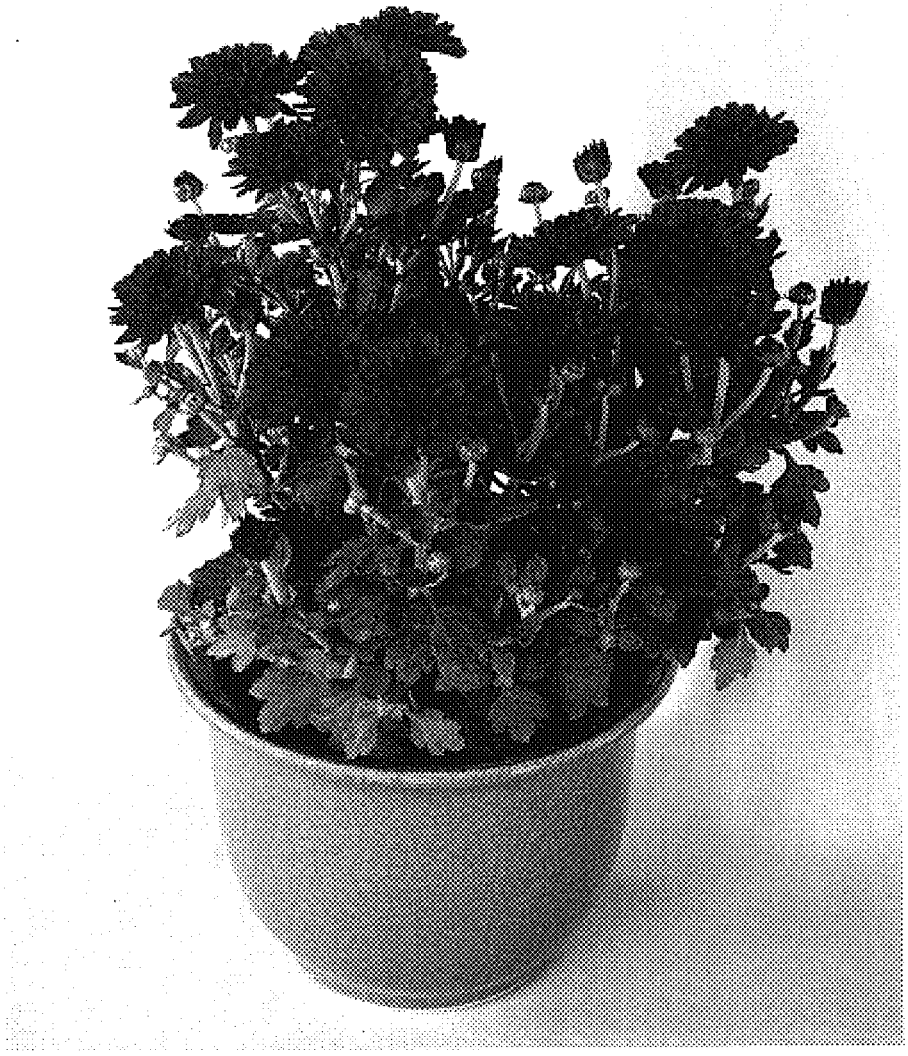

* * * * *